United States Patent
Wang et al.

(10) Patent No.: US 10,599,815 B2
(45) Date of Patent: Mar. 24, 2020

(54) METHOD AND SYSTEM FOR HEALTH CONDITION ANALYSIS BASED ON ELASTICITY DETECTION DEVICE

(71) Applicants: WUXI HISKY MEDICAL TECHNOLOGIES CO., LTD., Wuxi (CN); BEIJING FRIENDSHIP HOSPITAL, CAPITAL MEDICAL UNIVERSITY, Beijing (CN)

(72) Inventors: Yujuan Wang, Wuxi (CN); Jidong Jia, Wuxi (CN); Xiaojuan Ou, Wuxi (CN); Hong You, Wuxi (CN); Jinhua Shao, Wuxi (CN); Jin Sun, Wuxi (CN); Houli Duan, Wuxi (CN)

(73) Assignees: WUXI HISKY MEDICAL TECHNOLOGIES CO., LTD., Jiangsu (CN); BEIJING FRIENDSHIP HOSPITAL, CAPITAL MEDICAL UNIVERSITY, Beijing (CN)

( * ) Notice: Subject to any disclaimer, the term of this patent is extended or adjusted under 35 U.S.C. 154(b) by 0 days.

(21) Appl. No.: 15/649,528

(22) Filed: Jul. 13, 2017

(65) Prior Publication Data

US 2017/0308670 A1 Oct. 26, 2017

Related U.S. Application Data

(63) Continuation of application No. PCT/CN2015/081955, filed on Jun. 19, 2015.

(30) Foreign Application Priority Data

Feb. 12, 2015 (CN) .......................... 2015 1 0076104

(51) Int. Cl.
*G06F 19/00* (2018.01)
*G16H 40/67* (2018.01)
(Continued)

(52) U.S. Cl.
CPC .......... *G06F 19/3418* (2013.01); *A61B 8/485* (2013.01); *A61B 8/5223* (2013.01);
(Continued)

(58) Field of Classification Search
CPC ........ G16H 30/00; G16H 10/00; G16H 40/00; G16H 50/00; G01N 29/043; A61B 8/00
See application file for complete search history.

(56) References Cited

U.S. PATENT DOCUMENTS 5,564,423 A * 10/1996 Mele .................... A61B 8/0875
                                                      600/438
8,706,530 B2    4/2014 Ohnemus et al. ................. 705/3
(Continued)

FOREIGN PATENT DOCUMENTS

CN    101483690 A    7/2009
CN    202362780 U    8/2012
(Continued)

OTHER PUBLICATIONS

International Search Report of corresponding International PCT Application No. PCT/CN2015/081955, dated Nov. 18, 2015.
(Continued)

*Primary Examiner* — Peter Luong
(74) *Attorney, Agent, or Firm* — J.C. Patents

(57) ABSTRACT

The invention provides a method and system for health condition analysis based on an elasticity detection device. The method includes: sending, by a client, a health condition analysis request to a cloud server, where the health condition analysis request includes individual attribute identification information of a querier; acquiring, by the cloud server, to-be-analyzed data corresponding to the health condition analysis request from a cloud database storing displacement data of each querier, and conducting data analysis on the to-be-analyzed data to obtain health condition information
(Continued)

of the querier; and receiving, by the client, the health condition information of the querier sent by the cloud server. Therefore, by virtue of mass displacement data of mass queriers stored in the cloud server, the querier can conveniently learn his/her health condition in time through the client.

20 Claims, 2 Drawing Sheets

(51) Int. Cl.
*G16H 10/60* (2018.01)
*G16H 50/20* (2018.01)
*A61B 8/08* (2006.01)

(52) U.S. Cl.
CPC ............ *G16H 10/60* (2018.01); *G16H 40/67* (2018.01); *G16H 50/20* (2018.01)

(56) References Cited

U.S. PATENT DOCUMENTS

| | | | |
|---|---|---|---|
| 2004/0120557 A1* | 6/2004 | Sabol | G06Q 10/10 382/128 |
| 2006/0026040 A1* | 2/2006 | Reeves | G06F 19/321 705/3 |
| 2010/0036254 A1* | 2/2010 | Owsley | A61B 5/026 600/454 |
| 2010/0056877 A1 | 3/2010 | Fein et al. | 600/301 |
| 2011/0307269 A1* | 12/2011 | Benja-Athon | G06F 19/325 705/2 |
| 2013/0112557 A1 | 5/2013 | Javitt et al. | 204/403.01 |
| 2013/0208966 A1 | 8/2013 | Zhao et al. | 382/131 |
| 2013/0226604 A1 | 8/2013 | Etchegoyen | 705/2 |
| 2014/0046173 A1 | 2/2014 | Greenleaf et al. | |
| 2014/0142984 A1 | 5/2014 | Wright et al. | |
| 2014/0288425 A1* | 9/2014 | Shin | A61B 8/485 600/438 |
| 2014/0371617 A1 | 12/2014 | Muradia | 600/528 |
| 2015/0099960 A1* | 4/2015 | Ryu | A61B 8/4444 600/407 |

FOREIGN PATENT DOCUMENTS

| | | |
|---|---|---|
| CN | 103902836 A | 7/2014 |
| CN | 103905549 A | 7/2014 |
| CN | 104318057 A | 1/2015 |
| CN | 104337550 A | 2/2015 |
| CN | 104622513 A | 5/2015 |
| CN | 104636622 A | 5/2015 |
| EP | 0 912 957 B1 | 12/2004 |
| JP | 2003-022325 A | 1/2003 |
| JP | 2010-259806 A | 11/2010 |
| JP | 2011-104102 A | 6/2011 |
| JP | 2014-184145 A | 10/2014 |
| KR | 10-2013-0021929 | 3/2013 |
| KR | 10-2014-0120615 A | 10/2014 |
| RU | 123 649 U1 | 1/2013 |
| WO | WO 2011/004661 A1 | 1/2011 |

OTHER PUBLICATIONS

Chinese First Examination Report of corresponding Chinese patent Application No. 201510076104.5, dated Jan. 26, 2017.
The Japanese Examination Report of corresponding Japan patent application No. 2017-542171, dated Aug. 13, 2018.
The Brazilian Examination Report of corresponding Brazil patent application No. BR112017017201-1, dated Jun. 7, 2018.
The Russian Examination Report of corresponding Russian Federation patent application No. 2017131711/08(055611), dated Jul. 5, 2018.
"A Great Show of the Revolutionary Device and Method, which Leads the Future of the Image Diagnosis in 2014 Korean Society of Radiology by GE Healthcare" General Electric Press Releases in Korea; (Sep. 2018).
The extended European Search Report of corresponding European patent application No. 15881701.5-1126/3258404, dated Sep. 18, 2018.
The Korean Examination Report of corresponding Korea Republic of patent application No. 10-2017-7025523, dated Sep. 28, 2018.
The Japanese Notice of Allowance of correspondence Japan application No. 2017-0542171, dated Apr. 24, 2019.

* cited by examiner

METHOD AND SYSTEM FOR HEALTH CONDITION ANALYSIS BASED ON ELASTICITY DETECTION DEVICE

CROSS-REFERENCE TO RELATED APPLICATIONS

This application is a continuation of International Application No. PCT/CN2015/081955, filed on Jun. 19, 2015, which claims priority to Chinese Patent Application No. 201510076104.5, filed on Feb. 12, 2015, entitled "METHOD AND SYSTEM FOR HEALTH CONDITION ANALYSIS BASED ON ELASTICITY DETECTION DEVICE", both of which are hereby incorporated by reference in their entireties.

TECHNICAL FIELD

The present invention belongs to the field of data processing technologies, particularly to a method and a system for health condition analysis based on an elasticity detection device.

BACKGROUND

As medical technologies evolve by the day and stress in life continues to mount, people have heightened awareness about health.

Yet, a common way for people to get informed about their health condition is still going to hospitals for receiving various tests, such as elasticity detection on the viscoelastic medium, and obtaining the health condition of an individual through a doctor who analyzes the detection data of that individual. However, going to hospital for tests often fails to satisfy people's demands for real-time health condition tracking which provides, in a timely and convenient manner, knowledge about their physical conditions.

SUMMARY

According to the problems, the invention provides a method and a system for health condition analysis based on an elasticity detection device, so as to realize an objective of allowing individuals to get informed about his/her health condition through a client timely and conveniently.

A first aspect of embodiments of the present invention provides a method for health condition analysis based on an elasticity detection device, the elasticity detection device including an excitation apparatus for generating an elasticity shear wave in a viscoelastic medium and a capturing apparatus for determining displacement data which is generated by the viscoelastic medium under action of the elasticity shear wave, where the elasticity detection device sends the obtained displacement data to a cloud server for storage; and the method for health condition analysis includes:

sending, by a client, a health condition analysis request to the cloud server, where the health condition analysis request includes individual attribute identification information of a querier, so that the cloud server acquires to-be-analyzed data corresponding to the health condition analysis request from a cloud database, and conducts data analysis on the to-be-analyzed data to obtain health condition information of the querier, where the to-be-analyzed data includes the displacement data of a viscoelastic medium acquired by the querier through detection of the elasticity detection device; and receiving, by the client, the health condition information of the querier sent by the cloud server.

In a first possible implementation of the first aspect, the health condition analysis request further includes group attribute identification information of the querier;

where the health condition analysis request is further used such that the cloud server acquires, from the cloud database, a first displacement data set corresponding to the group attribute identification information, and conducts data analysis on the first displacement data set to obtain a first analysis result; and such that the cloud server acquires, from the cloud database, a second displacement data set corresponding to the individual attribute identification information, conducts data analysis on the second displacement data set to obtain a second analysis result, and obtains health condition information corresponding to the second analysis result according to the first analysis result.

According to the first aspect or the first possible implementation thereof, in a second possible implementation of the first aspect, the method further includes:

receiving, by the client, health advice information sent by the cloud server, where the health advice information is determined by the cloud server according to the health condition information.

According to the first aspect or the first possible implementation thereof, in a third possible implementation of the first aspect, the group attribute identification information includes at least one of the following identifications: identification of a disease to be queried, identification of an age bracket, and identification of gender.

A second aspect of embodiments of the present invention provides another method for health condition analysis based on an elasticity detection device, the elasticity detection device including an excitation apparatus for generating an elasticity shear wave in a viscoelastic medium and a capturing apparatus for determining displacement data which is generated by the viscoelastic medium under action of the elasticity shear wave, where the elasticity detection device sends the obtained displacement data to a cloud server for storage; and the method for health condition analysis includes:

receiving, by the cloud server, a health condition analysis request sent by a client, where the health condition analysis request includes individual attribute identification information of a querier;

acquiring, by the cloud server, to-be-analyzed data corresponding to the health condition analysis request from a cloud database, and conducting data analysis on the to-be-analyzed data to obtain health condition information of the querier, where the to-be-analyzed data includes the displacement data of a viscoelastic medium acquired by the querier through detection of the elasticity detection device; and sending, by the cloud server, the health condition information of the querier to the client.

In a first possible implementation of the second aspect, the health condition analysis request further includes group attribute identification information of the querier;

the acquiring, by the cloud server, to-be-analyzed data corresponding to the health condition analysis request from a cloud database, and conducting data analysis on the to-be-analyzed data to obtain health condition information of the querier includes:

acquiring, by the cloud server and from the cloud database, a first displacement data set corresponding to the group attribute identification information, and conducting data analysis on the first displacement data set to obtain a first analysis result;

acquiring, by the cloud server and from the cloud database, a second displacement data set corresponding to the individual attribute identification information, and conducting data analysis on the second displacement data set to obtain a second analysis result; and obtaining, by the cloud server, health condition information corresponding to the second analysis result according to the first analysis result.

According to the second aspect or the first possible implementation thereof, in a second possible implementation of the second aspect, the method further includes:

determining, by the cloud server, health advice information according to the health condition information; and sending, by the cloud server, the health advice information to the client.

According to the second aspect or the first possible implementation thereof, in a third possible implementation of the second aspect, the group attribute identification information includes at least one of the following identifications: identification of a disease to be queried, identification of an age bracket, and identification of gender.

A third aspect of embodiments of the present invention provides a system for health condition analysis based on an elasticity detection device, the elasticity detection device including an excitation apparatus for generating an elasticity shear wave in a viscoelastic medium and a capturing apparatus for determining displacement data which is generated by the viscoelastic medium under action of the elasticity shear wave, where the elasticity detection device sends the obtained displacement data to a cloud server for storage; and the system includes: a client and the cloud server;

the client is configured to send a health condition analysis request to the cloud server, the health condition analysis request includes individual attribute identification information of a querier;

the cloud server is configured to receive the health condition analysis request sent by the client, acquire to-be-analyzed data corresponding to the health condition analysis request from a cloud database, and conduct data analysis on the to-be-analyzed data to obtain health condition information of the querier, where the to-be-analyzed data includes the displacement data of a viscoelastic medium acquired by the querier through detection of the elasticity detection device; and the cloud server is further configured to send the health condition information of the querier to the client.

In a first possible implementation of the third aspect, the health condition analysis request further includes group attribute identification information of the querier;

the cloud server is further configured to acquire, from the cloud database, a first displacement data set corresponding to the group attribute identification information, and conduct data analysis on the first displacement data set to obtain a first analysis result;

the cloud server is further configured to acquire, from the cloud database, a second displacement data set corresponding to the individual attribute identification information, and conduct data analysis on the second displacement data set to obtain a second analysis result; and the cloud server is further configured to obtain health condition information corresponding to the second analysis result according to the first analysis result.

According to the third aspect or the first possible implementation thereof, in a second possible implementation of the third aspect, the cloud server is further configured to determine health advice information according to the health condition information, and send the health advice information to the client; and the client is further configured to receive the health advice information.

According to the method and system for health condition analysis based on the elasticity detection device provided by the present invention, displacement data obtained by every elasticity detection device for every individual person is stored on the cloud end. Accordingly, a querier can send, via a client provided on a terminal device, a health condition analysis request to a cloud server, and the cloud server can retrieve, from a cloud database storing displacement data of each querier, to-be-analyzed data corresponding to individual attribute information of the querier in the health condition analysis request, and conduct data analysis on the to-be-analyzed data to obtain health condition information of the querier, such as a variation trend about organ elasticity of the querier, or the probability of the querier in catching a certain disease. Therefore, by leveraging mass data stored in the cloud server, the querier can conveniently learn his/her health condition in time through the client.

DETAILED DESCRIPTION

In order to make objectives, technical solutions and advantages of embodiments of the present invention clearer, the technical solutions in the embodiments of the present invention will be described hereunder clearly and comprehensively with reference to accompanying drawings. Obviously, the described embodiments are only a part of embodiments of the present invention, rather than all of them. Any and all other embodiments obtained by persons of ordinary skill in the art based on the presently disclosed embodiments without making any creative effort shall fall into the protection scope of the present invention.

Figure 1:
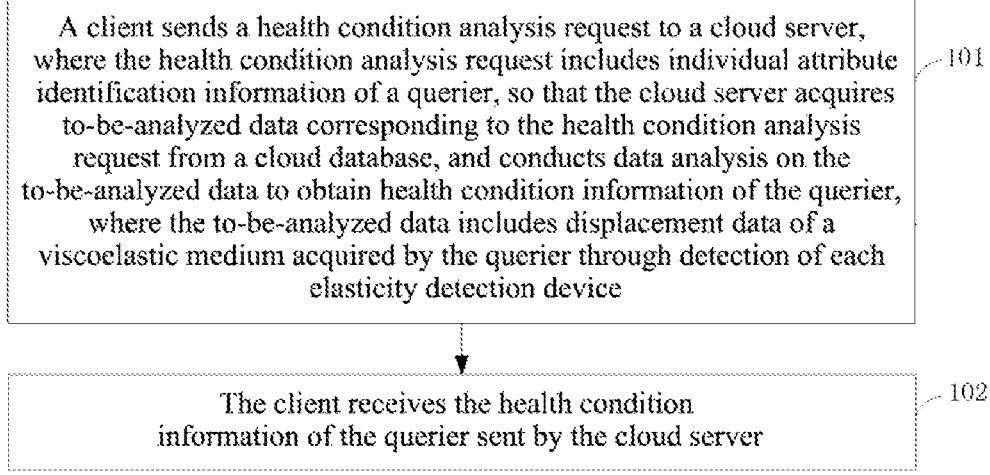
FIG. 1 is a flowchart of a method for health condition analysis based on an elasticity detection device according to the first embodiment of the present invention.

FIG. 1 is a flowchart of a method for health condition analysis based on an elasticity detection device according to the first embodiment of the present invention. In this embodiment, the elasticity detection device performs elasticity detection on a physical body to obtain displacement data thereof, where the displacement data is obtained by the elasticity detection device via performing elasticity detection on a viscoelastic medium of the detection taker, and every elasticity detection device sends the displacement data thus obtained to a cloud server for storage. The elasticity detection device includes: an excitation apparatus for generating an elasticity shear wave in the viscoelastic medium of the detection taker; and a capturing apparatus for determining displacement data which is generated by the viscoelastic medium under action of the elasticity shear wave. In this case, the operation principal of the excitation apparatus and capturing apparatus can be summarized as: the excitation apparatus excites a shear wave, which is equivalent to generating a vibration signal, towards the viscoelastic medium on the surface of a viscoelastic organ medium, e.g. a liver; the viscoelastic medium vibrates under the action of the vibration signal, so that the capturing apparatus can send an ultrasonic signal into the viscoelastic medium, and the viscoelastic medium will generate an echo response according to elastic mechanics principles. Since the viscoelastic organ medium has different elastic stress or elastic strain under different conditions, e.g. a normal condition or a pathological condition, the capturing apparatus can calculate and obtain the displacement data of the viscoelastic medium according to echo signals before and after the application of pressure. The displacement data reflects elastic characteristics of the viscoelastic organ, and can serve as an important reference in determining physical health condition. In this embodiment, different detection takers may receive detection using different elasticity detection devices at different time, and each elasticity detection device will obtain the displacement data of the detection taker and upload the same to the cloud server for cloud-end storage. As depicted in FIG. 1, the method in this embodiment includes:

Step 101: a client sends a health condition analysis request to a cloud server, wherein the health condition analysis request includes individual attribute identification information of a querier, so that the cloud server acquires to-be-analyzed data corresponding to the health condition analysis request from a cloud database, and conducts data analysis on the to-be-analyzed data to obtain health condition information of the querier, wherein the to-be-analyzed data includes displacement data of a viscoelastic medium acquired by the querier through detection of each elasticity detection device;

Step 102: the client receives the health condition information of the querier sent by the cloud server.

The client described in this embodiment is provided in a user terminal, wherein the user terminal refers to a terminal device, e.g. a smartphone, a laptop, a tablet and the like, of the querier who desires to query about his/her health condition, and the client may be in the form of, e.g., an APP, a Web and the like. The user terminal device to which the client belongs may be connected with the cloud server via a wired connection, or a wireless connection such as WLAN, 3G, 4G, GRPS and the like, which are not limited herein.

In this embodiment, the cloud server stores the displacement data obtained via elasticity detection performed on viscoelastic organ medium, e.g. the liver, by individual queriers at different time and locations. In addition, the displacement data includes, for instance, personal identification information, such as name, age, personal ID, contact information and the like, of the detection taker, and a displacement value obtained via the detection, and may further include, e.g., identification information of the elasticity detection device performing the detection, information of the hospital offering the elasticity detection device, and information of the doctor operating the elasticity detection device and the like. Therefore, this embodiment leverages mass displacement data of mass users stored in a cloud database on the cloud server to realize health condition tracking for queriers, helping the queriers to be timely and conveniently informed of their individual physical conditions.

In particular, when a querier desires to query about his/her health condition, the querier may send a health condition analysis request to the cloud server via the client, where the health condition analysis request includes individual attribute identification information of the querier. The individual attribute identification information is used for uniquely identifying the querier, and may be, e.g., a personal ID, name, contact information and the like, of the querier. When the client is formed as a web page, the querier may input associated individual attribute identification via, e.g., an input prompt box on a page following the prompt. When the health condition analysis request carrying individual attribute identification information of the querier sent by the client is received, the cloud server queries the cloud database thereof and obtain to-be-analyzed data corresponding to the individual attribute identification information, where the to-be-analyzed data includes displacement data of a viscoelastic medium obtained by the querier via detection of elasticity detection devices.

The to-be-analyzed data of the querier is a set of displacement data which is obtained through elasticity detection for multiple times taken by the querier during a period of time. The cloud server analyzes the set of displacement data to obtain an analysis result. wherein the analysis performed by the cloud server on the set of displacement data may be, for example, a trend chart analyzing displacement values of the querier, i.e., a chart showing the trend of the displacement values changing over time; as another example, the analysis performed by the cloud server on the set of displacement data may be performing statistical analysis on the number of times that the displacement value exceeds a certain threshold within a certain time interval and corresponding displacement values. It's worth noting that the analysis result obtained by the cloud server via performing the above described analysis on the to-be-analyzed data may be taken as a type of health condition information for the querier. Thus, the cloud server sends the analysis result to the client, so that the querier can be informed about his/her health condition information.

In this embodiment, displacement data of every individual person which is obtained through detection is stored on the cloud end by every elasticity detection device, so that the querier can send, via the client provided on his/her terminal device, the health condition analysis request to the cloud server, and the cloud server can retrieve, from the cloud database storing displacement data of each querier, to-be-analyzed data corresponding to the individual attribute information of the querier in the health condition analysis request, and conduct data analysis on the to-be-analyzed data to obtain health condition information of the querier, such as a variation trend about organ elasticity of the querier, or the probability of the querier in catching a disease or the like. Therefore, by leveraging mass data stored in the cloud server, the querier can conveniently learn his/her health condition in time through the client.

Further, on the basis of the above embodiment, it is further desired to consider how the group attribute information of the querier impacts the health condition analysis result, in order to improve accuracy with respect to the health condition information of the querier which is obtained by the cloud server through analyzing. In short, for instance, considering a trend chart based on the same set of displacement data, if the set of displacement data corresponds to detection data of a child, the health condition of the child which is reflected by this trend chart may indicate good health condition; if the set of displacement data corresponds to detection data of an elderly person, the health condition of the elderly person which is reflected by this trend chart may indicate poor health condition. Therefore, impacts from the group attribute information of the querier over the health condition analysis result need to be considered.

In particular, the health condition analysis request sent by the client to the cloud server further includes, in addition to the individual attribute identification information of the querier, group attribute identification information of the querier, where the group attribute identification information includes at least one of the following identifications: identification of a disease to be queried, identification of an age bracket, and identification of gender, where the identification of the age bracket may be, e.g. four predefined age brackets: child, teenager, young and middle-aged adult, and senior adult, with each age bracket corresponding to a different range of age. The identification of the disease may be, for instance, identification of a liver disease, such as liver cirrhosis, fatty liver and the like.

In particular, after the health condition analysis request carrying individual attribute identification information and group attribute identification information of the querier is received from the client, on one hand, the cloud server retrieves from the cloud database a first displacement data set corresponding to the group attribute identification information, and conducts data analysis on the first displacement data set to obtain a first analysis result; on another hand, the cloud server further retrieves from the cloud database a second displacement data set corresponding to the individual attribute identification information, and conducts data analysis on the second displacement data set to obtain a second analysis result. Based on previously described analysis procedure, the procedure through which the cloud server analyzes the first displacement data set and second displacement data set will not be repeated herein.

In this case, when the group attribute identification information is identification of a certain disease, the first displacement data set is displacement data, which meets certain requirements, of all individuals who undergo detection for this kind of disease. It's worth noting that, in case that elasticity detection is taken as an example in this embodiment, the aforementioned disease particularly refers to a disease associated with elasticity detection results, such as the previously illustrated fatty liver and liver cirrhosis and the like. Therefore, the displacement data included in the data set corresponding to this disease is required to meet requirements corresponding to this disease. For instance, the elastic displacement typically falls in a value range of a1-a2 for disease A; and the elastic displacement typically falls in a value range of b1-b2 for disease B.

It's worth noting that, in case that the group attribute identification information is, e.g., identification of a certain disease and identification of a certain age bracket, the first analysis result may be a consolidated trend chart of displacement data, of the group in this age bracket, corresponding to this disease. Accordingly, the second analysis result may be a trend chart of displacement data, of the querier, corresponding to this disease. In this case, it can be understood that the age of the querier is within the age bracket in the group attribute identification information.

After obtaining the first analysis result and second analysis result through analyzing, the cloud server obtains, according to the first analysis result, health condition information corresponding to the second analysis result. That is, health condition reflected by the second analysis result is determined by referring to the first analysis result. In particular, the first analysis result indicates an analysis result for a certain group type to which the querier belongs and/or for a certain disease. By referring to the analysis result for the group, assessment can be made more accurately with regard to the health condition of the querier as indicated by the analysis result for the individual querier. Illustratively, for example, an analysis result on displacement data of an individual querier shows that all displacement values of the querier fall in a range of A-B. Meanwhile, an analysis result on displacement data of a corresponding group, e.g., a group in a certain age bracket, indicates that displacement values of those in the age bracket fall in a range of C-D, and the range A-B falls near the middle portion within the range C-D. Therefore, by referring to the analysis result of the group, the cloud server determines that the individual querier is of good health condition, and returns this health condition information to the client. It's worth noting that, in this embodiment, the health condition information of the querier, for instance, merely indicates the probability of the querier in potentially catching a certain disease.

Further, after assessing and determining the health condition information of the querier, the cloud server may further push corresponding health advice information, e.g. advice on health management and other public welfare information and the like, to the querier based on the health condition. Accordingly, in the above Step 102, the client can, in addition to receiving the health condition information of the querier sent by the cloud server, further receive health advice information sent by the cloud server. Illustratively, the health condition information indicates, e.g., the querier has poor liver elasticity, and the cloud server may push health advice information about, e.g., diet tips and workout strategies. It's worth noting that the push service of the cloud server is customizable. That is, the cloud server pushes relevant health advice to the client after performing the health condition analysis, if the client has subscribed to the health advice push service of the cloud server.

Figure 2:
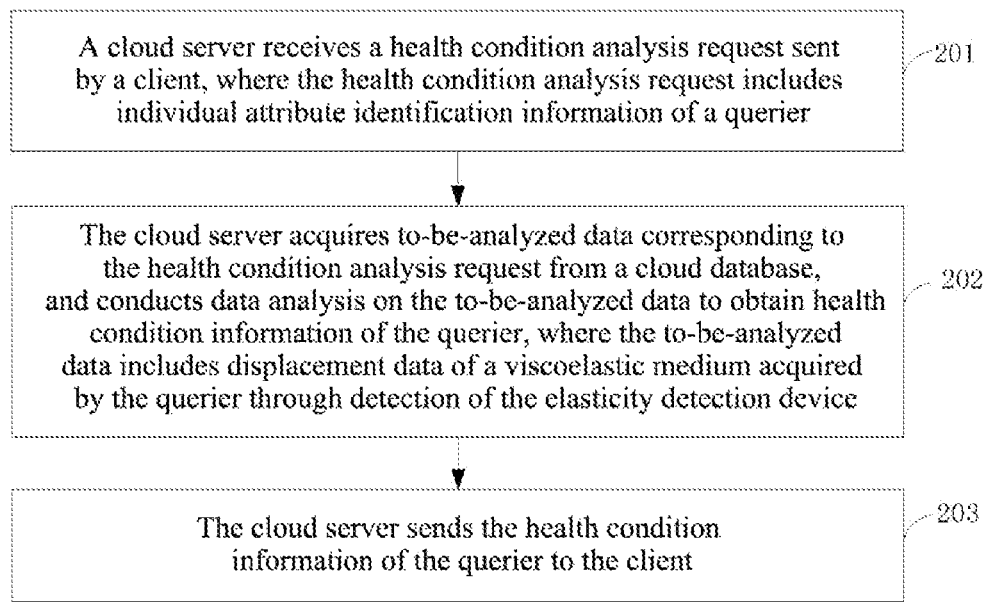
FIG. 2 is a flowchart of a method for health condition analysis based on an elasticity detection device according to the second embodiment of the present invention.

FIG. 2 is a flowchart of a second embodiment of a method for health condition analysis based on an elasticity detection device according to the present invention. As depicted in FIG. 2, the method includes:

Step 201: a cloud server receives a health condition analysis request sent by a client, where the health condition analysis request includes individual attribute identification information of a querier.

Step 202: the cloud server acquires to-be-analyzed data corresponding to the health condition analysis request from a cloud database, and conduct data analysis on the to-be-analyzed data to obtain health condition information of the querier, where the to-be-analyzed data includes displacement data of a viscoelastic medium acquired by the querier through detection of the elasticity detection device.

Step 203: the cloud server sends the health condition information of the querier to the client.

In this embodiment, the displacement data is obtained, and the elasticity detection device is configured, in the same way as those in the embodiment depicted in FIG. 1, which will not be repeated herein.

The cloud server stores the displacement data obtained via elasticity detection performed on viscoelastic organ media, e.g. the liver, by individual queriers at different time and locations. In addition, the displacement data includes, for instance, personal identification information, such as name, age, personal ID, contact information and the like, of the detection taker, and a displacement value obtained via the detection, and may further include, e.g., identification information of the elasticity detection device performing the detection, information of the hospital offering the elasticity detection device, and information of the doctor operating the elasticity detection device and the like. In particular, the cloud server may store the displacement data, e.g., under various categories, such as creating different databases according to, e.g., different hospitals or regions, or defining different storage spaces within the same database. The categories may also be based on identification of certain diseases. Additionally, during the storage process, displacement data of the same detection taker for the same disease is stored at a centralized location, so that storage efficiency can be improved, while subsequent data querying can be facilitated. Of course, the data may also be stored according to a time sequence.

When the querier desires to query and learn about his/her health condition, the querier can send the health condition analysis request containing individual attribute identification information of the querier to the cloud server via the client. When the health condition analysis request is received, the cloud server queries the cloud database thereof and obtains to-be-analyzed data corresponding to the individual attribute identification information, i.e. a set of all displacement data about the querier.

The cloud server analyzes the set of displacement data to obtain an analysis result, where the analysis performed by the cloud server on the set of displacement data may be, for example, a trend chart analyzing displacement values of the querier, i.e., a chart showing the trend of the displacement values changing over time. It's worth noting that the analysis result obtained by the cloud server via performing the above described analysis on the to-be-analyzed data may be taken as a type of health condition information for the querier. Thus, the cloud server sends the analysis result to the client, so that the querier can be informed about his/her health condition information.

Further, on the basis of the above embodiment, it is further desired to consider how the group attribute information of the querier impacts the health condition analysis result, in order to improve accuracy with respect to the health condition information of the querier which is obtained by the cloud server through analyzing. In particular, the health condition analysis request sent by the client to the cloud server further includes, in addition to the individual attribute identification information of the querier, group attribute identification information of the querier, where the group attribute identification information includes at least one of the following identifications: identification of a disease to be queried, identification of an age bracket, and identification of gender, where the meaning of the foregoing identification information is detailed by way of example in the embodiment depicted in FIG. 1, which will not be repeated herein.

After the health condition analysis request carrying individual attribute identification information and group attribute identification information of the querier is received from the client, on one hand, the cloud server retrieves from the cloud database a first displacement data set corresponding to the group attribute identification information, and conducts data analysis on the first displacement data set to obtain a first analysis result; on another hand, the cloud server further retrieves from the cloud database a second displacement data set corresponding to the individual attribute identification information, and conducts data analysis on the second displacement data set to obtain a second analysis result. Based on previously described analysis procedure, the procedure through which the cloud server analyzes the first displacement data set and second displacement data set will not be repeated herein. In case that the group attribute identification information is, e.g., identification of a certain disease and identification of a certain age bracket, the first analysis result may be a consolidated trend chart of displacement data, of the group in this age bracket, corresponding to this disease. Accordingly, the second analysis result may be a trend chart of displacement data, of the querier, corresponding to this disease. In this case, it can be understood that the age of the querier is within the age bracket in the group attribute identification information.

After obtaining the first analysis result and second analysis result through analyzing, the cloud server obtains, according to the first analysis result, health condition information corresponding to the second analysis result. That is, health condition reflected by the second analysis result is determined by referring to the first analysis result. In particular, the first analysis result indicates an analysis result for a certain group type to which the querier belongs and/or for a certain disease. By referring to the analysis result for the group, assessment can be made more accurately with regard to the health condition of the querier as indicated by the analysis result for the individual querier. Illustratively, for example, an analysis result on displacement data of an individual querier shows that all displacement values of the querier fall in a range of A-B. Meanwhile, an analysis result on displacement data of a corresponding group, e.g., a group in a certain age bracket, indicates that displacement values of those in the age bracket fall in a range of C-D, and the range A-B falls near the middle portion within the range C-D. Therefore, by referring to the analysis result of the group, the cloud server determines that the individual querier is of good health condition, and returns this health condition information to the client. It's worth noting that, in this embodiment, the health condition information of the querier, for instance, merely indicates the probability of the querier in potentially catching a certain disease.

Further, after assessing and determining the health condition information of the querier, the cloud server may further push corresponding health advice information, e.g. advice on health management and other public welfare information and the like, to the querier based on the health condition. Accordingly, in the aforementioned Step 203, the cloud server further sends, in addition to the health condition information of the querier, health advice information to the client.

In this embodiment, the querier sends, via the client provided on his/her terminal device, the health condition analysis request to the cloud server, and the cloud server can retrieve, from the cloud database storing displacement data of each querier, the to-be-analyzed displacement data set corresponding to the individual attribute information of the querier in the health condition analysis request, and conduct data analysis on the to-be-analyzed displacement data set to obtain health condition information of the querier, such as a variation trend about organ elasticity of the querier, or the probability of the querier in potentially catching a certain disease. Therefore, by virtue of mass detection data of mass queriers stored in the cloud server, the querier can conveniently learn his/her comprehensive health condition in time through the client.

Figure 3:
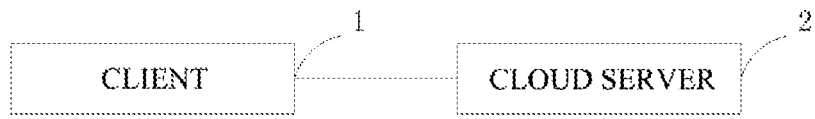
FIG. 3 is a schematic structural diagram of a health condition analysis system based on an elasticity detection device according to an embodiment of the present invention.

FIG. 3 is a schematic structural diagram of an embodiment of a health condition analysis system based on an elasticity detection device according to the present invention. As depicted in FIG. 3, the system includes: a client 1 and a cloud server 2.

The client 1 is configured to send a health condition analysis request to the cloud server, the health condition analysis request includes individual attribute identification information of a querier.

The cloud server 2 is configured to receive the health condition analysis request sent by the client, acquire to-be-analyzed data corresponding to the health condition analysis request from a cloud database, and conduct data analysis on the to-be-analyzed data to obtain health condition information of the querier, where the to-be-analyzed data includes displacement data of a viscoelastic medium acquired by the querier through detection of the elasticity detection device.

The cloud server 2 is further configured to send the health condition information of the querier to the client.

In this case, the elasticity detection device includes: an excitation apparatus for generating an elasticity shear wave in a viscoelastic medium; and a capturing apparatus for determining displacement data which is generated by the viscoelastic medium under action of the elasticity shear wave. Additionally, the elasticity detection device sends the obtained displacement data to the cloud server for storage.

Further, the health condition analysis request also includes group attribute identification information of the querier.

The cloud server 2 is further configured to acquire, from the cloud database, a first displacement data set corresponding to the group attribute identification information, and conduct data analysis on the first displacement data set to obtain a first analysis result.

The cloud server 2 is further configured to acquire, from the cloud database, a second displacement data set corresponding to the individual attribute identification information, and conduct data analysis on the second displacement data set to obtain a second analysis result.

The cloud server 2 is further configured to obtain health condition information corresponding to the second analysis result according to the first analysis result.

Further, the cloud server 2 is further configured to determine health advice information according to the health condition information, and send the health advice information to the client.

The client 1 is further configured to receive the health advice information.

The system provided in this embodiment can be used for performing the method of embodiment depicted in FIG. 1 or FIG. 2 following similar principals and producing similar technical effects, which will not be repeated herein.

Persons of ordinary skill in the art may understand that, all or a part of steps of the foregoing method embodiments may be implemented by a program instructing relevant hardware. The program may be stored in a computer readable storage medium. When the program runs, the steps of the foregoing method embodiments are performed. The foregoing storage medium includes various mediums capable of storing program codes, such as a ROM (read only memory), a RAM (random access memory), a magnetic disk, or an optical disc.

Finally, it should be noted that foregoing embodiments are merely intended for describing, rather than limiting, the technical solutions of the present invention. Although the present invention is described in detail with reference to the foregoing embodiments, persons of ordinary skill in the art should understand that they may still make modifications to the technical solutions described in the foregoing embodiments, or make equivalent replacements to some or all technical features therein; however, these modifications or replacements do not make the essence of corresponding technical solutions depart from the scope of the technical solutions in the embodiments of the present invention.

What is claimed is:

1. A method for health condition analysis of a displacement data generated by an elasticity detection device, the elasticity detection device comprising an excitation apparatus and a capturing apparatus, and the method for health condition analysis of the displacement data generated by the elasticity detection device comprising:

generating, by the excitation apparatus, an elasticity shear wave in a viscoelastic medium;

determining, by the capturing apparatus, displacement data which is generated by the viscoelastic medium under action of the elasticity shear wave;

sending, by the elasticity detection device, the displacement data to a cloud server for storing in a cloud database;

sending, by a client provided on a terminal device, a health condition analysis request to the cloud server, wherein the health condition analysis request comprises individual attribute identification information of a querier and group attribute identification information of the querier, wherein the group attribute identification information of the querier comprises at least one of identification of a disease to be queried, identification of an age bracket and identification of gender, and the individual attribute identification information of the querier comprises personal identification information;

receiving, by the cloud server, the health condition analysis request sent by the client;

acquiring, by the cloud server and from the cloud database, a first displacement data set corresponding to the group attribute identification information, and conducting, by the cloud server, data analysis on the first displacement data set to obtain a first analysis result wherein the first displacement data set comprises first displacement data which is obtained via an elasticity detection performed on viscoelastic mediums of a plurality of individuals and which is corresponding to the at least one of identification of the disease to be queried, identification of the age bracket and identification of the gender;

acquiring, by the cloud server and from the cloud database, a second displacement data set corresponding to the individual attribute identification information, and conducting, by the cloud server, data analysis on the second displacement data set to obtain a second analysis result, wherein the second displacement data set comprises second displacement data which is obtained via the elasticity detection performed on a viscoelastic medium of the querier and which is corresponding to the personal identification information;

obtaining, by the cloud server, health condition information of the viscoelastic medium of the querier corresponding to the second analysis result according to the first analysis result;

sending, by the cloud server, the health condition information of the viscoelastic medium of the querier to the client; and receiving, by the client, the health condition information of the viscoelastic medium of the querier sent by the cloud server.

2. The method according to claim 1, wherein the method further comprises:

receiving, by the client, health advice information sent by the cloud server, wherein the health advice information is determined by the cloud server according to the health condition information of the viscoelastic medium of the querier.

3. The method according to claim 1, wherein the personal identification information comprises at least one of name, age, personal ID, contact information of the querier, and the individual attribute identification information of the querier further comprises at least one of identification information of the elasticity detection device performing the detection, information of a hospital offering the elasticity detection device, and information of a doctor operating the elasticity detection device.

4. The method according to claim 1, wherein the group attribute identification information is identification of the disease, and the acquiring, by the cloud server and from the cloud database, the first displacement data set corresponding to the group attribute identification information comprises acquiring, by the cloud server and from the cloud database, displacement data of individuals who undergo detection for the disease corresponding to the group attribute identification information.

5. The method according to claim 1, wherein the group attribute identification information is identification of the disease and identification of the age bracket, and the conducting, by the cloud server, data analysis on the first displacement data set to obtain the first analysis result comprises conducting, by the cloud server, data analysis on the first displacement data set to obtain a consolidated trend chart of the displacement data, of the group in the age bracket, corresponding to the disease.

6. The method according to claim 1, wherein the conducting, by the cloud server, data analysis on the second displacement data set to obtain the second analysis result comprises conducting, by the cloud server, data analysis on the second displacement data set to obtain a trend chart analyzing displacement data of the querier changing over time.

7. The method according to claim 1, wherein the conducting, by the cloud server, data analysis on the second displacement data set to obtain the second analysis result comprises conducting, by the cloud server, data analysis on the second displacement data set to obtain a number of times that the displacement data exceeds a threshold within a time interval and the displacement data exceeding the threshold within the time interval.

8. A method for health condition analysis of a displacement data generated by an elasticity detection device, the elasticity detection device comprising an excitation apparatus and a capturing apparatus, and the method for health condition analysis of the displacement data generated by the elasticity detection device comprising:

generating, by the excitation apparatus, an elasticity shear wave in a viscoelastic medium;

determining, by the capturing apparatus, displacement data which is generated by the viscoelastic medium under action of the elasticity shear wave;

sending, by the elasticity detection device, the displacement data to a cloud server for storing in a cloud database;

receiving, by the cloud server, a health condition analysis request sent by a client, wherein the health condition analysis request comprises individual attribute identification information of a querier and group attribute identification information of the querier, wherein the group attribute identification information of the querier comprises at least one of identification of a disease to be queried, identification of an age bracket and identification of gender, and the individual attribute identification information of the querier comprises personal identification information;

acquiring, by the cloud server and from the cloud database, a first displacement data set corresponding to the group attribute identification information, and conducting, by the cloud server, data analysis on the first displacement data set to obtain a first analysis result, wherein the first displacement data set comprises first displacement data which is obtained via an elasticity detection performed on viscoelastic mediums of a plurality of individuals and which is corresponding to the at least one of identification of the disease to be queried, identification of the age bracket and identification of the gender;

acquiring, by the cloud server and from the cloud database, a second displacement data set corresponding to the individual attribute identification information, and conducting, by the cloud server, data analysis on the second displacement data set to obtain a second analysis result, wherein the second displacement data set comprises second displacement data which is obtained via the elasticity detection performed on a viscoelastic medium of the querier and which is corresponding to the personal identification information;

obtaining, by the cloud server, health condition information of the viscoelastic medium of the querier corresponding to the second analysis result according to the first analysis result;

sending, by the cloud server, the health condition information of the viscoelastic medium of the querier to the client.

9. The method according to claim 8, wherein the method further comprises:

determining, by the cloud server, health advice information according to the health condition information of the viscoelastic medium of the querier; and sending, by the cloud server, the health advice information to the client.

10. The method according to claim 8, wherein the personal identification information comprises at least one of name, age, personal ID, contact information of the querier, and the individual attribute identification information of the querier further comprises at least one of identification information of the elasticity detection device performing the detection, information of a hospital offering the elasticity detection device, and information of a doctor operating the elasticity detection device.

11. The method according to claim 8, wherein the group attribute identification information is identification of the disease, and the acquiring, by the cloud server and from the cloud database, the first displacement data set corresponding to the group attribute identification information comprises acquiring, by the cloud server and from the cloud database, displacement data of individuals who undergo detection for the disease corresponding to the group attribute identification information.

12. The method according to claim 8, wherein the group attribute identification information is identification of the disease and identification of the age bracket, and the conducting, by the cloud server, data analysis on the first displacement data set to obtain the first analysis result comprises conducting, by the cloud server, data analysis on the first displacement data set to obtain a consolidated trend chart of the displacement data, of the group in the age bracket, corresponding to the disease.

13. The method according to claim 8, wherein the conducting, by the cloud server, data analysis on the second displacement data set to obtain the second analysis result comprises conducting, by the cloud server, data analysis on the second displacement data set to obtain a trend chart analyzing displacement data of the querier changing over time.

14. The method according to claim 8, wherein the conducting, by the cloud server, data analysis on the second displacement data set to obtain the second analysis result comprises conducting, by the cloud server, data analysis on the second displacement data set to obtain a number of times that the displacement data exceeds a threshold within a time interval and the displacement data exceeding the threshold within the time interval.

15. A system for health condition analysis of a displacement data generated by an elasticity detection device, the elasticity detection device comprising an excitation apparatus and a capturing apparatus, and the system comprises: the elasticity detection device, a client and the cloud server;
  the excitation apparatus is configured to generate an elasticity shear wave in a viscoelastic medium;
  the capturing apparatus is configured to determine displacement data which is generated by the viscoelastic medium under action of the elasticity shear wave;
  the elasticity detection device is configured to send the displacement data to a cloud server for storing in a cloud database;
  the client is configured to send a health condition analysis request to the cloud server, the health condition analysis request comprising individual attribute identification information of a querier and group attribute identification information of the querier, wherein the group attribute identification information of the querier comprises at least one of identification of a disease to be queried, identification of an age bracket and identification of gender, and the individual attribute identification information of the querier comprises personal identification information;
  the cloud server is configured to:
    receive the health condition analysis request sent by the client;
    acquire, from the cloud database, a first displacement data set corresponding to the group attribute identification information, and conduct data analysis on the first displacement data set to obtain a first analysis result, wherein the first displacement data set comprises first displacement data which is obtained via an elasticity detection performed on viscoelastic mediums of a plurality of individuals and which is corresponding to the at least one of identification of the disease to be queried, identification of the age bracket and identification of the gender;
    acquire, from the cloud database, a second displacement data set corresponding to the individual attribute identification information, and conduct data analysis on the second displacement data set to obtain a second analysis result, wherein the second displacement data set comprises second displacement data which is obtained via the elasticity detection performed on a viscoelastic medium of the querier and which is corresponding to the personal identification information;
    obtain health condition information of the viscoelastic medium of the querier corresponding to the second analysis result according to the first analysis result; and
    send the health condition information of the viscoelastic medium of the querier to the client; and
  the client is further configured to receive the health condition information of the viscoelastic medium of the querier sent by the cloud server.

16. The system according to claim 15, wherein the cloud server is further configured to determine health advice information according to the health condition information of the viscoelastic medium of the querier, and send the health advice information to the client; and
  the client is further configured to receive the health advice information.

17. The system according to claim 15, wherein the group attribute identification information is identification of the disease, and
  the cloud server is configured to acquire, from the cloud database, displacement data of individuals who undergo detection for the disease corresponding to the group attribute identification information.

18. The system according to claim 15, wherein the group attribute identification information is identification of the disease and identification of the age bracket, and
  the cloud server is configured to conduct data analysis on the first displacement data set to obtain a consolidated trend chart of the displacement data, of the group in the age bracket, corresponding to the disease.

19. The system according to claim 15, wherein the cloud server is configured to conduct data analysis on the second displacement data set to obtain a trend chart analyzing displacement data of the querier changing over time.

20. The system according to claim 13, wherein the cloud server is configured to conduct data analysis on the second displacement data set to obtain a number of times that the displacement data exceeds a threshold within a time interval and the displacement data exceeding the threshold within the time interval.

* * * * *